United States Patent [19]

Keeling

[11] Patent Number: 4,995,384

[45] Date of Patent: Feb. 26, 1991

[54] NECK SUPPORT FOR NASAL CANNULA

[76] Inventor: James L. Keeling, 5939 S. Newland St., Littleton, Colo. 80123

[21] Appl. No.: 429,071

[22] Filed: Oct. 30, 1989

[51] Int. Cl.⁵ ............................................. A61M 15/08
[52] U.S. Cl. ................................ 128/207.18; 128/912; 128/DIG. 26; 128/204.18
[58] Field of Search ...................... 128/207.18, 207.17, 128/912, DIG. 26, 207.14, 207.15; 604/94

[56] References Cited

U.S. PATENT DOCUMENTS

| | | |
|---|---|---|
| 1,115,702 | 11/1914 | Luxmore . |
| 2,735,432 | 2/1956 | Hudson . |
| 3,039,469 | 6/1962 | Fountain . |
| 3,513,844 | 5/1970 | Smith . |
| 4,106,505 | 8/1978 | Salter et al. . |
| 4,249,529 | 2/1981 | Nestor et al. . |
| 4,331,143 | 5/1982 | Foster . |
| 4,351,331 | 9/1982 | Gereg . |
| 4,367,735 | 1/1982 | Dali . |
| 4,378,012 | 3/1983 | Brown . |
| 4,406,283 | 9/1983 | Bir . |
| 4,480,639 | 11/1984 | Peterson et al. . |
| 4,537,192 | 8/1985 | Foster . |
| 4,559,941 | 12/1985 | Timmons et al. . |
| 4,592,351 | 6/1986 | Smith et al. . |
| 4,641,646 | 2/1987 | Schultz et al. . |
| 4,658,814 | 4/1987 | Anderson . |
| 4,666,432 | 5/1987 | McNeish et al. . |
| 4,774,944 | 10/1988 | Mischinski ................... 128/207.17 |
| 4,915,104 | 4/1990 | Marcy ......................... 128/207.18 |

Primary Examiner—Edgar S. Burr
Assistant Examiner—Stephen Funk
Attorney, Agent, or Firm—Duane Burton

[57] ABSTRACT

An improved neck support for a nasal cannula assembly. The neck support includes a support bracket having a central opening therethrough for receiving and engaging a main oxygen supply conduit of the nasal cannula assembly to attach the nasal cannula assembly to the support bracket. The central opening includes an access slot for the main oxygen supply conduit. The neck support further includes a flexible chain which attaches to the support bracket and which can be placed loosely around a patient's neck. In use, the neck support can be rested against the patient's body and supported by the flexible chain about the patient's neck such that a substantial portion of the weight of the nasal cannula assembly is borne by the patient's neck.

2 Claims, 1 Drawing Sheet

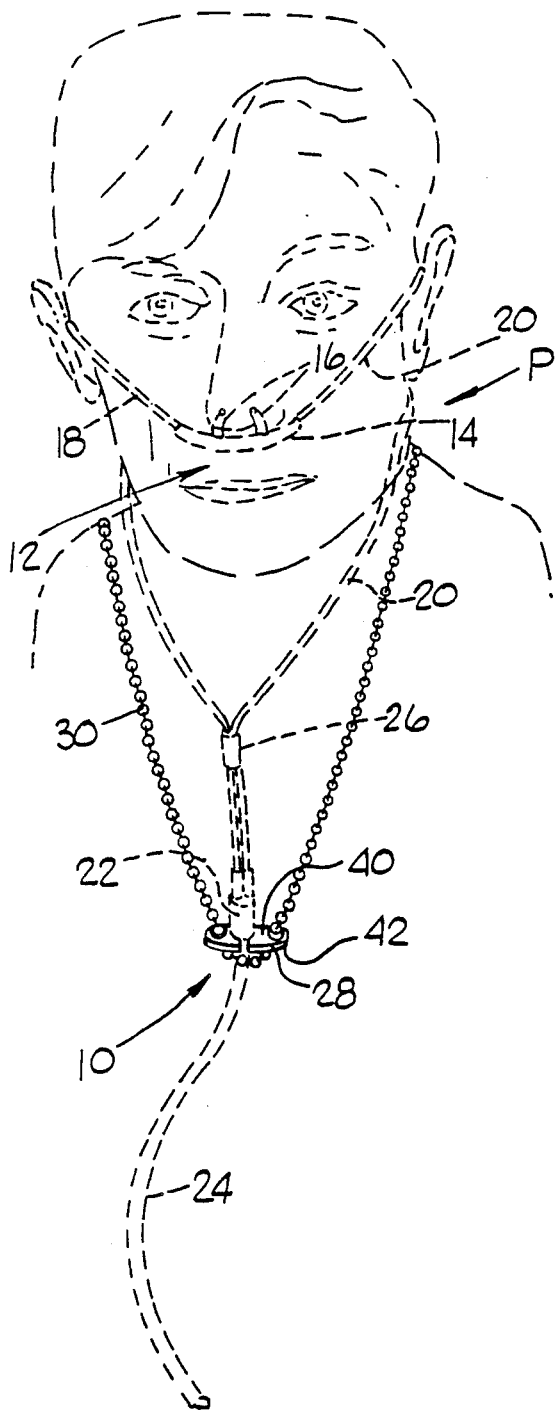
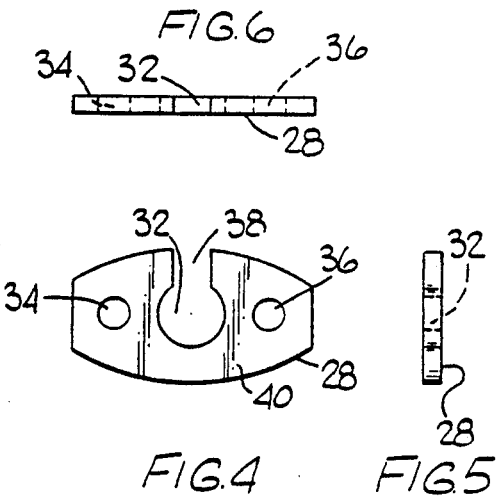
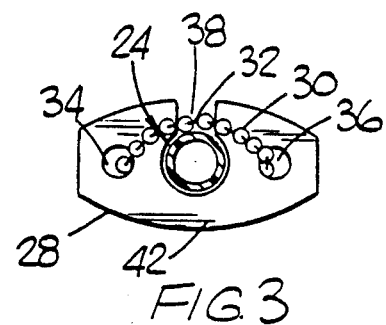
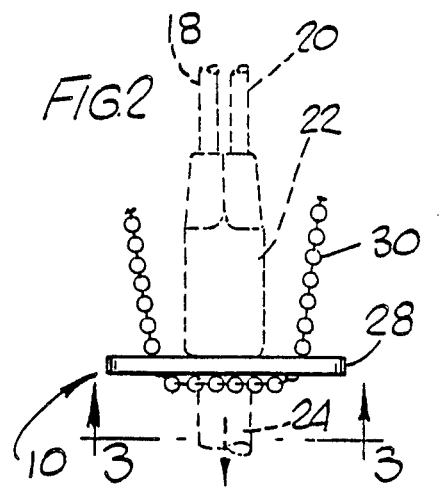

NECK SUPPORT FOR NASAL CANNULA

TECHNICAL FIELD

This invention relates to medical equipment for supporting medical tubes and more particularly to an improved neck support for use with a nasal cannula assembly.

BACKGROUND ART

Medical patients having respiratory problems are often required to wear a nasal cannula assembly which supplies oxygen or other fluid directly into the nasal passages. The nasal cannula assembly includes a nasal cannula which is placed on the nasalabidial area of a patient. The nasal cannula includes nasal extensions or tips which extend into and contact the patient's nostrils. The nasal cannula assembly may also include one or usually two oxygen supply tubes. The oxygen supply tubes are usually soft and flexible tubes that attach at either end of the nasal cannula. The oxygen supply tubes are typically placed across the patient's face, over and behind the ears, down the jaw area and then brought together under the chin. A suitable connector or coupling connects the oxygen supply tubes to a main oxygen supply conduit.

With this arrangement the weight of the nasal cannula assembly is supported largely by the ears and face of the patient. Any movement of the patient's head tends to bend and twist the oxygen supply tubes and main oxygen supply conduit and causes discomfort and irritation of the patient's ears and face. In addition movement of the head may displace the nasal tips of the nasal cannula from the patient's nostrils and decrease the efficiency of the nasal cannula. These problems are compounded by patients who are mobile or ambulatory.

In the past it has been common practice to tape the oxygen supply tubes of the nasal cannula assembly to the patient's face with adhesive tape. The tape however, may cause further discomfort and irritation for the patient and may also inhibit function of the nasal cannula.

Several devices have heretofore been proposed as an aid in positioning a nasal cannula on a patient's face. Similar devices have also been proposed for use with tracheotomy and endotracheal tubes.

U.S. Pat. No. 4,480,639 to Peterson for instance, discloses a tube retaining device that straps to a patient's face and includes a pair of clamps for positioning a nasal cannula adjacent a patient's nostrils.

U.S. Pat. No. 4,367,735 to Dali discloses a nasal cannula that attaches to a skull cap and secures nasal prongs to the nasal passages of a patient.

U.S. Pat. No. 3,039,469 to Fountain discloses a tracheotomy tube support that includes a tube retaining plate and a neckband for the patient.

U.S. Pat. No. 4,658,814 to Anderson discloses an endotracheal tube holder that includes a support for the tube which extends over the ears and under the chin of a patient.

These patents are representative of the art. Nothing, however, has heretofor provided a completely satisfactory support for a nasal cannula. Some assemblies require the patient to be stationary and cannot be utilized by ambulatory or mobile patients. Others put excessive strain on a patient's ears or face or inhibit the function of the nasal cannula. Accordingly, it is an object of this invention to provide an improved neck support for a nasal cannula assembly.

SUMMARY OF THE INVENTION

In accordance with the present invention an improved neck support for a nasal cannula assembly is provided. The neck support is intended for use with a nasal cannula assembly that may include a nasal cannula, a pair of oxygen supply tubes that are connected to the nasal cannula and placed around the patient's ears, and a main oxygen supply conduit to the nasal cannula. The neck support simply stated, comprises a support bracket and a flexible chain which transfers a substantial portion of the weight of the nasal cannula assembly along with loads caused by movement of the nasal cannula assembly to a patient's neck.

The support bracket includes a central opening therethrough for engaging the main oxygen supply conduit to the nasal cannula. This attaches the nasal cannula assembly to the support bracket. The central opening of the support bracket is formed with an access slot for allowing access of the main oxygen supply conduit into the central opening. A pair of chain mounting holes through the support bracket on either side of the central opening are provided for securing the flexible chain to the support bracket.

In use of the neck support, the nasal cannula is placed on a patient's nasalabidial area with the nasal tips engaging the nostrils. The oxygen supply tubes for the nasal cannula attach on either side of the nasal cannula. The oxygen supply tubes are placed from the nasal cannula across the face, over and around the ears and along the patient's jaw and terminate at a tube coupling under the chin. The tube coupling attaches the oxygen supply tubes to the main oxygen supply conduit of the nasal cannula.

The main oxygen supply conduit can be inserted through the access slot into the central opening of the support bracket with the central opening engaging and abutting the resilient walls of the main oxygen supply conduit and with the flexible chain preventing movement of the main oxygen supply conduit out of the central opening. The support bracket in turn rests against the patient's body attached to the flexible chain. The flexible chain is placed loosely around the patient's neck. The nasal cannula assembly is thus attached to the support bracket and the weight of the nasal cannula assembly is borne largely by the patient's neck rather than the ears. In addition, movement by the patient and loads caused by movement of the nasal cannula assembly are transferred through the flexible chain to the patient's neck such that there is less discomfort to the patient and the nasal cannula better stays in position on the nasalabidial area of the patient.

Additional advantages of this invention will become apparent from the description which follows taken in conjunction with the accompanying drawing.

BRIEF DESCRIPTION OF THE DRAWING

FIG. 1 is a perspective view of a neck support for a nasal cannula assembly constructed in accordance with the invention and shown in use on a patient;

FIG. 2 is a partial side elevation view of the neck support and the associated portions of the nasal cannula assembly;

FIG. 3 is a cross sectional view taken along the line 3—3 of FIG. 2;

FIG. 4 is a top view of a support bracket component for the neck support constructed in accordance with the invention;

FIG. 5 is a side view of FIG. 4; and

FIG. 6 is a back view of FIG. 4.

DESCRIPTION OF THE PREFERRED EMBODIMENT

Referring now to FIG. 1 an improved neck support constructed in accordance with the invention is shown and generally designated as 10. The neck support 10 is intended for use with a nasal cannula assembly 12 illustrated in position on the face of a patient P.

The nasal cannula assembly 12 includes a hollow tubular nasal cannula 14 which rests on the nasalabidial area of the patient's face. A pair of nasal tips 16 extend from the nasal cannula 14 into the patient's nostrils. The nasal cannula assembly 12 also includes a pair of oxygen supply tubes 18, 20 connected to either side of the nasal cannula 14.

The oxygen supply tubes 18, 20 are soft flexible tubes and are placed across the patient's face, over and around the ears and along the jaw. The oxygen supply tubes 18, 20 terminate at a tube coupling 22 under the patient's chin. The tube coupling 22 connects the oxygen supply tubes 18, 20 to a main oxygen supply conduit 24. The main oxygen supply conduit 24 is also formed from soft flexible plastic tubing material having resilient walls as is common for such medical devices. The nasal cannula assembly 12 also includes a slip loop 26 for positioning and adjusting the location of the oxygen supply tubes 18, 20 under the patient's chin.

The neck support 10 of the invention attaches to the main oxygen supply conduit 24 of the nasal cannula assembly 12 under the patient's chin. The neck support 10 generally stated, comprises support means, in the form of a support bracket 28 for supporting the nasal cannula assembly 12, and neck securing means in the form of a flexible chain 30 for securing the support bracket 28 to the patient's neck.

The support bracket 28 is shown separately in FIGS. 4-6. The support bracket 28 is a flat generally rectangular shaped plate having curved sides and rounded corners and edges. In general, the support bracket is formed such that there are no sharp edges to contact the patient. The support bracket may be machined, stamped or molded as a unitary structure from a cleanable and corrosion resistant material such as metal or plastic. The support bracket 28 includes a first attachment means for attaching the nasal cannula assembly 12 and a second attachment means for attaching the flexible chain 30.

The first attachment means is in the form of a central opening 32 through the approximate center of the support bracket 28. The central opening 32 receives the main oxygen supply conduit 24 of the nasal cannula assembly 12 and attaches the nasal cannula assembly 12 to the support bracket 28. The second attachment means of the support bracket 28 is in the form of chain mounting holes 34, 36 through the support bracket 28 equally spaced on either side of the central opening 32 for attaching the flexible chain 30.

The central opening 32 of the support bracket 28 is sized to receive the main oxygen supply conduit 24 of the nasal cannula 14 and engage the resilient walls of the main oxygen supply conduit 24 in an abutting relationship. As shown in FIG. 4 the central opening 32 is formed with an access slot 38 through the support bracket 28 which allows the main oxygen supply conduit 24 of the nasal cannula assembly 12 to be placed into the central opening 32. The access slot 38 is sized with a width that is less than the diameter of the central opening 32.

As previously stated, the main oxygen supply conduit 24 of the nasal cannula assembly 12 is fabricated from a material such as soft flexible plastic tubing. The central opening 32 is sized to be approximately equal to or slightly smaller in diameter than the outside diameter of the main oxygen supply conduit 24. The main oxygen supply conduit 24 can thus be pressed through the access slot 38 into the central opening 32 and maintained in an abutting relationship with the central opening 32 by the resiliency of the material and walls of the main oxygen supply conduit 24. The location of the main oxygen supply conduit 24 within the central opening 32 is clearly shown in FIG. 3. Additionally, as shown in FIG. 3, the flexible chain 30 can be placed across access slot 38 of the central opening 32 and against the main oxygen supply conduit 24 to prevent movement of the main oxygen supply conduit 24 out of the central opening 32.

As shown in FIG. 1, in use the support bracket 28 can be rested against the patient's body in the upper chest or neck area of the patient, and positioned along the main oxygen supply conduit 24 at a desired location. The support bracket 28 may be located for instance, with an upper surface 40 of the support bracket 28 contacting and abutting the tube coupling 22 for the nasal cannula assembly 10. The tube coupling 22 thus functions as a stop means for limiting axial movement of the support bracket 28 in one direction along the main oxygen supply conduit 24.

Referring now to FIG. 4, the chain mounting holes 34, 36 for attaching the flexible chain 30 to the support bracket 28, are located through the support bracket 28 equally spaced on either side of the central opening 32 of the support bracket 28. The chain mounting holes 34, 36 are sized to receive the flexible chain 30, while allowing movement of the flexible chain 30 within the chain mounting holes 34, 36. The diameters of the chain mounting holes 34, 36 are equal to one another and approximately equal to but slightly greater than the outside diameter of the flexible chain 30.

The flexible chain 30 is formed as an endless loop, which as shown in FIG. 3, is threaded through the chain mounting holes 34, 36 of the support bracket 28, and across a lower surface 42 of the support bracket 28. The flexible chain 30 also crosses the access slot 38 of the central opening 32 of the support bracket 28 to prevent movement of the main oxygen supply conduit 24 out of the central opening 32. With this arrangement the flexible chain 30 can be looped loosely around the patient's neck, as shown in FIG. 1, to secure the support bracket 28 and nasal cannula assembly 12 to the patient's neck. The flexible chain 30 is preferably fabricated from a cleanable corrosion resistant material such as beaded metal chain that slides easily on the patient's neck with a minimum of irritation. Moreover, the flexible chain is sized to fit loosely rather than tightly around the patient's neck such that the support bracket can rest against the patient's body in approximately the upper chest and neck area. Alternately, in place of a flexible chain 30 other suitable flexible neck securing means such as flexible straps, or surgical tubing may also be utilized.

In use of the neck support 10 of the invention, the flexible chain 30 is placed loosely around the patient's neck. The support bracket 28 rests against the patient's body attached to and supported by the flexible chain 30. The main oxygen supply conduit 24 of the nasal cannula 14 is attached to the central opening 32 of the support bracket 28 with the location of the flexible chain 30 preventing movement of the main oxygen supply conduit 24 out of the central opening 32. A large portion of the weight of the nasal cannula assembly 12 is thus transferred from a patient's ears and face to his neck. This arrangement is generally more comfortable and less irritating to a patient. Additionally, with the neck support 10 of this invention, movement of the head and body of the patient tends to provide less bending, twisting and movement of the components of the nasal cannula assembly 12 because loads and movements are transferred or absorbed at the patient's neck.

The invention has been described in detail with particular reference to a preferred embodiment thereof, but it will be understood that variations and modifications can be effected within the spirit and scope of the invention.

What is claimed is:

1. In a nasal cannula assembly having a nasal cannula and having a pair of supply tubes connected to the nasal cannula and placed over and around a patient's ears and neck connected below the patient's chin to a main supply conduit, a neck support comprising:

a support bracket including a central opening therethrough for engaging the main supply conduit of the nasal cannula assembly and an access slot portion therethrough for providing access for the main supply conduit into the central opening;

neck securing means attached to said support bracket for placement loosely around the patient's neck said neck securing means comprising an endless loop of flexible chain that is placed across the access slot of said support bracket to prevent movement of the main supply conduit out of the central opening; and said support bracket includes chain mounting openings through said support bracket located on either side of said central opening for attaching said flexible chain to said support bracket;

whereby the weight of the nasal cannula assembly and said support bracket are supported largely by said neck securing means.

2. A neck support as claimed in claim 1 and wherein:

a surface of said support bracket may contact a tube coupling attached to the main supply conduit of the nasal cannula assembly to limit axial movement of said support bracket along the main supply conduit.

* * * * *